(12) United States Patent
Penman et al.

(10) Patent No.: US 7,195,739 B1
(45) Date of Patent: Mar. 27, 2007

(54) AROMATIC CONTAINER HEATER

(76) Inventors: Marilyn F. Penman, 5050 N. Waterfall Dr., Pleasant View, UT (US) 84414; Richard E. Penman, 5050 N. Waterfall Dr., Pleasant View, UT (US) 84414

( * ) Notice: Subject to any disclaimer, the term of this patent is extended or adjusted under 35 U.S.C. 154(b) by 388 days.

(21) Appl. No.: 10/606,042

(22) Filed: Jun. 25, 2003

Related U.S. Application Data

(60) Provisional application No. 60/391,379, filed on Jun. 26, 2002.

(51) Int. Cl.
*H05B 3/54* (2006.01)
*A61L 9/02* (2006.01)

(52) U.S. Cl. .................. 422/123; 422/125; 219/674; 219/236; 219/424; 219/427

(58) Field of Classification Search ............... 422/123, 422/124, 125; 219/209, 481, 385, 674, 236, 219/424, 427, 549
See application file for complete search history.

(56) References Cited

U.S. PATENT DOCUMENTS

| | | | |
|---|---|---|---|
| 3,839,006 A * | 10/1974 | Pikor | 65/174 |
| 4,137,833 A | 2/1979 | Yelloz | 99/293 |
| 4,346,059 A | 8/1982 | Spector | 422/125 |
| 4,595,564 A | 6/1986 | Spector et al. | 422/125 |
| 4,634,838 A | 1/1987 | Berz | 219/297 |
| 5,138,138 A * | 8/1992 | Theilacker et al. | 219/528 |
| 5,651,942 A | 7/1997 | Christensen | 422/125 |
| 5,831,242 A * | 11/1998 | Gallagher | 219/202 |
| 6,254,836 B1 | 7/2001 | Fry | 422/124 |
| 6,394,848 B1 * | 5/2002 | Beideman | 439/622 |
| 6,413,476 B1 * | 7/2002 | Barnhart | 422/124 |
| 6,516,142 B2 | 2/2003 | Grant et al. | 392/451 |
| 6,539,171 B2 | 3/2003 | VonArx et al. | 392/451 |
| 6,548,015 B1 | 4/2003 | Stubbs et al. | 422/5 |

\* cited by examiner

*Primary Examiner*—Krisanne Jastrzab
*Assistant Examiner*—Sean Conley
(74) *Attorney, Agent, or Firm*—Lloyd W. Sadler; James L. Sonntag

(57) ABSTRACT

An aromatic container heater and assembly adapted to enhance the release of desirable scent from an aromatic or fragrant candle by heating the exterior of a candle container and thereby melting the candle to release the desired scent. The heater includes a conductor, held within an insulating cover, which is electrically connected to an AC plug for receiving a current and thereby generating the necessary heat to melt the candle.

12 Claims, 3 Drawing Sheets

AROMATIC CONTAINER HEATER

CROSS REFERENCE TO RELATED APPLICATIONS

This application is based on U.S. Provisional Application Ser. No. 60/391,379, which was filed on Jun. 26, 2002, and priority is claimed thereto.

BACKGROUND OF INVENTION

1. Field of the Invention

This invention relates to devices for releasing a scent or fragrance from a scented candle. More specifically, this invention relates to devices for releasing a scent or fragrance from a scented candle that employs an electric heating element to warm or melt the scented candle.

2. Description of the Related Art

A variety of devices and techniques are well known for heating a scented candle. As candles typically have a wick, it is known to light the wick to heat the scented candle. The disadvantage of this technique is that as the wick is burned the candle is used up. It is also known to place the candle, in its container, on an electric heater or warmer. The disadvantage of this approach is that the wax or gel is heated from the bottom and that the scent is not generally released until the top surface is liquefied. A number of other devices that use heat to enhance the release of a scent are known and described in the following U.S. patent documents, which although not necessarily meeting the statutory requirements of prior art are each hereby incorporated by references in its entirety for the material contained therein: U.S. Pat. Nos. 4,137,833, 4,346,059, 4,595,564, 4,634,838, 5,651,942, 6,254,836, 6,516,142, 6,539,171, and 6,548,015.

SUMMARY OF INVENTION

It is desirable to provide a device for the heating of scented candle, or the like, held within a heat conducting container. It is particularly desirable to provide a device for the heating of a scented candle that provides distributed heat about the exterior of the container to facilitate rapid and uniform heating and thereby an efficient release of the scent. Moreover, it is desirable to provide such a heating device that is designed to accommodate a wide variety of different sized and shaped standard scented candles.

Accordingly, it is an object of this invention to provide a device for the heating of a scented candle that has a heating element, which is flexible and configurable to fit around the container of a scented candle.

It is another object of this invention to provide a device for the heating of a scented candle that includes an electric heating element adapted to be placed in contact with the exterior surface of a scented candle container.

Another object of this invention is to provide a device for the heating of a scented candle that includes a safety enclosure about the heating element.

A further object of some embodiments of this invention is to provide a device for the heating of a scented candle that includes fuse to electrically protect the plugged in heating element.

A still further object of this invention is to provide a device for the heating of a scented candle that includes a standard plug for connection into an AC outlet.

Additional objects, advantages and other novel features of this invention will be set forth in part in the description that follows and in part will be apparent to those skilled in the art upon examination of the following or may be learned with the practice of the invention. The objects and advantages of this invention may be realized and attained by means of the instrumentalities and combinations particularly pointed out in the appended claims. Still other objects of the present invention will become readily apparent to those skilled in the art from the following description wherein there is shown and described present preferred embodiments of the invention, simply by way of illustration of the best modes currently known to carry out this invention. As it will be realized, this invention is capable of other different embodiments, and its several components, details, and specific components, dimensions and materials, are capable of modification in various aspects without departing from the invention. Accordingly, the drawings and descriptions should be regarded as illustrative in nature and not as restrictive.

BRIEF DESCRIPTION OF DRAWINGS

The accompanying drawings incorporated in and forming a part of the specification, illustrate embodiments of the present invention. Some, although not all, alternative embodiments are described in the following description.

In the drawings.

Reference will now be made in detail to the present preferred embodiments of the invention, examples of which are illustrated in the accompanying drawings.

DETAILED DESCRIPTION

The invention is a heater device for heating a scented candle to enhance the deployment of the aroma from the candle. Scented candles have been developed to release a desirable aroma from the candle as it is heated. Typically, the scented candles are provided with a wick, although heating the candle by burning the wick has substantial disadvantages, including that the candle becomes used up over time and that the release of the aroma is uneven. The scented candles are generally contained within a glass jar or other similar heat conducting material. This invention provides heat to the candle by wrapping a conductor about the exterior of the candle container. The conductor is attached to an AC plug, which when plugged into a standard AC outlet, provides a current through the conductor, causing the conductor to heat up. The heated conductor heats the candle container, thereby heating the candle material, typically wax or gel, which when melted releases an aroma from the candle. The present embodiment of the invention includes a heat and electricity insulating cover located about the area of the conductor not intended to be in contact with the candle container. In some embodiments, a fuse is provided in series with the conductor to provide electrical safety measures.

Figure 1:
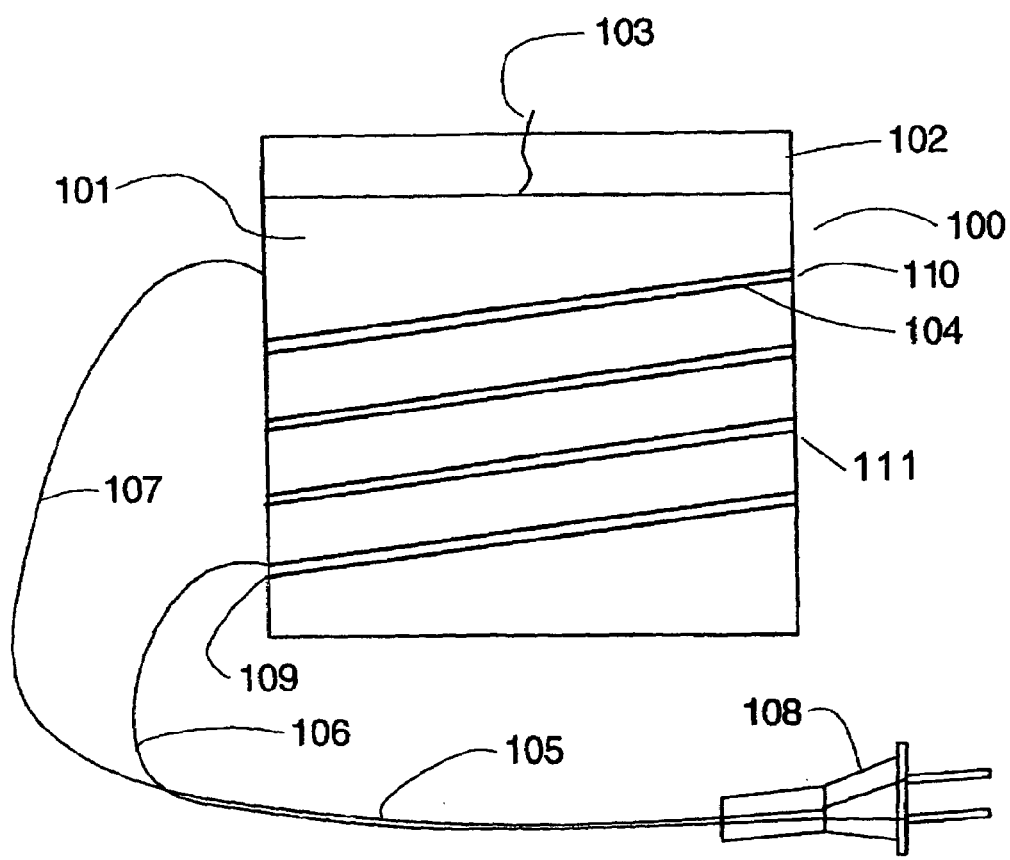
FIG. 1 is side view of a present embodiment of the invention wrapped about the container of a scented candle.

Referring now to FIG. 1, which is a side view of the present embodiment of the invention 100 wrapped about a candle container. The candle 101 is held within a container 102. The present candle 101 is an aromatic candle composed of wax, gel or the like. The container 102 is presently a glass jar, glass, cup, bowl or the like. The materials of the container 102 should be relatively resistant to heat deformation while being a good conductor of heat; therefore certain metals and ceramics may be substituted for glass as the container material. The typical candle 101 generally includes a wick 103, although the presence of a wick is not required for use with this invention. The conductor assembly 104 is shown wrapped about the exterior of a side wall 111 the candle container 102. Although shown here wrapping around the container 102 four times, the number of times that the conductor assembly 104 goes around the container 102 depends on the length of the conductor assembly 104 and the circumference of the container 102. In some instances the conductor assembly 104 may circle the container 102 many times and in other instances the conductor assembly 104 may not extend complete around the container 102 even once. The conductor assembly 104 is connected at a first end 109 to a first electrical conductor 106 and is connected at a second end 110 to a second electrical conductor 107. The first 106 and second 107 electrical conductors a formed together into an electrical cord 105, which in turn is connected to a standard electrical plug 108 adapted for insertion into a standard wall outlet.

Figure 2:
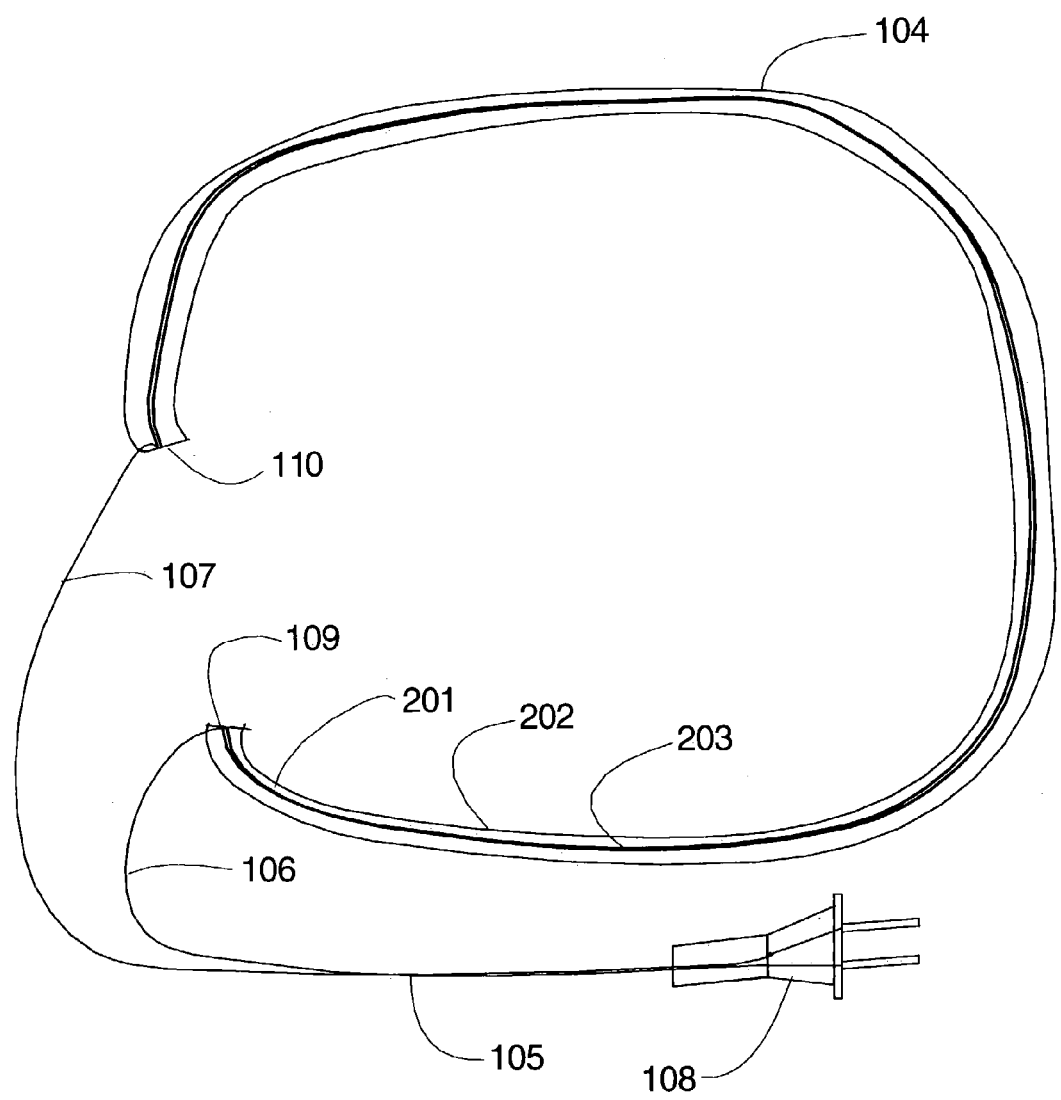
FIG. 2 is a detailed drawing of the present embodiment of the invention.

FIG. 2 shows the aromatic container heater of this invention with additional detail of the conductor assembly 104, specifically the conductor 201 and the insulating cover 202. In the present embodiment of the invention the conductor 201 is a bendable copper tube, although in alternative envisioned embodiments, the bendable copper tube can be substituted with a stranded cable, a mesh, a chain or another bendable but moderately rigid metal devices. Also, the material used in the conductor 201 can be substituted with another other electrical/heat conducting material, including, but not necessarily limited to, aluminum, tin, silver and gold. The first end 109 of the conductor assembly 104 is shown with the first electrical conductor 106 electrically connected to the conductor 201 and the second end 110 of the conductor assembly 104 is shown with the second electrical conductor 107 electrically connected to the other end of the conductor 201. The insulating cover 202 is adapted to cover the portion of the conductor 201 that is not intended to be in contact with the candle container 102. A portion 203 of the conductor 201 remains exposed for direct contact with the candle container 102. The present preferred insulating cover 202 is composed of plastic, although other electrical and heat insulating materials, including rubber, cloth, paper, wound glass, mica and the like can be substituted without departing from the concept of this invention.

Figure 3:
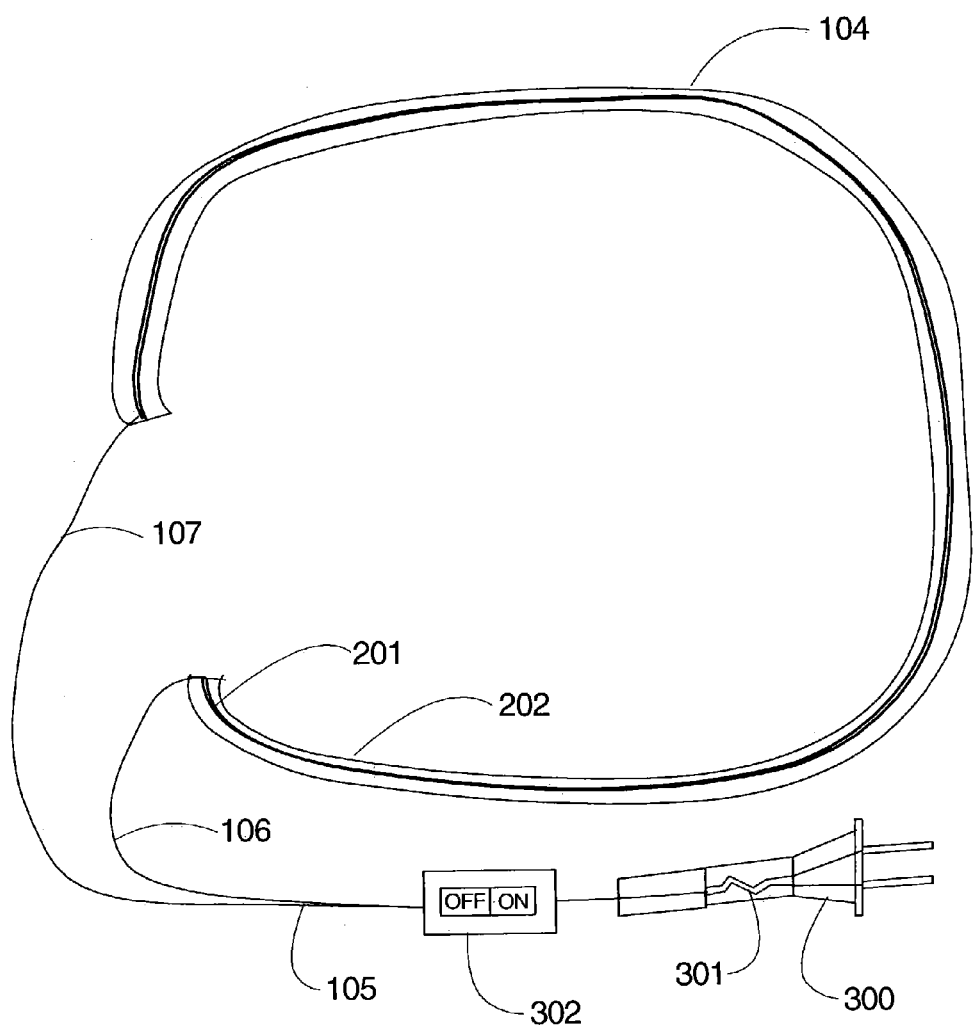
FIG. 3 is a detailed drawing of an alternative embodiment of the invention with fuse installed.

FIG. 3 shows the embodiment of the invention that includes an in-line fuse 301 electrically connected between the plug 300 and the electrical cord 105 to provide an electrical safety feature to the invention and an ON/OFF switch 302 also in-line between the plug 300 and the heat conductor 201.

It is to be understood that the above described and referenced embodiments and examples are merely illustrative of numerous and varied other embodiments and applications which may constitute applications of the principles of this invention. These example embodiments are not intended to be exhaustive or to limit the invention to the precise form, connection or choice of components or materials disclosed herein as the present preferred embodiments. Obvious modifications or variations are possible and foreseeable in light of the above teachings. These embodiments of the invention were chosen and described to provide the best illustration of the principles of the invention and its practical application to thereby enable one of ordinary skill in the art to make and use the invention, without undue experimentation. Other embodiments may be readily devised by those skilled in the art without departing from the spirit or scope of this invention and it is the intent of the inventor that they be deemed to be within the scope of this invention, as determined by the appended claims when they are interpreted in accordance with the breadth to which they are fairly legally and equitably entitled.

The invention claimed is:

1. An aromatic container heater assembly, comprising:
   (A) a heat-conducting candle container, having an interior and an exterior;
   (B) an aromatic candle including an aroma within said interior of said candle container;
   (C) a flexible and configurable conductor assembly, having a first end and a second end, said conductor assembly wrapped about and in contact with the exterior surface at a side wall of said candle container;
   (D) a first electrical conductor electrically connected to said first end of said conductor assembly;
   (E) a second electrical conductor electrically connected to said second end of said conductor assembly; and
   (F) an electrical plug electrically connected to said first electrical conductor and said second electrical conductor such that the flexible and configurable conductor assembly can heat the container sufficient to heat the candle to release aroma.

2. An aromatic container heater assembly, as recited in claim 1, wherein said conductor assembly further comprises a conductor.

3. An aromatic container heater assembly, as recited in claim 2, wherein said conductor assembly further comprises an insulating cover covering a portion of said conductor.

4. An aromatic container heater assembly, as recited in claim 2, wherein said conductor is composed of an electrical conducting material selected from the group consisting of copper, aluminum, tin, silver, gold, nickel, chromium and alloys thereof.

5. An aromatic container heater assembly, as recited in claim 3, wherein said conductor is composed of an electrical insulator selected from the group consisting of plastic, rubber, cloth, paper, glass, mica and combinations thereof.

6. An aromatic container heater assembly, as recited in claim 2, wherein said conductor is bendable.

7. An aromatic container heater assembly, as recited in claim 2, wherein said conductor is a device selected from the group consisting of a bendable tube, a stranded cable, a mesh, a chain, a thermal polymer and a ceramic tube.

8. An aromatic container heater assembly, as recited in claim 1, wherein said container further comprises a heat conducting receptacle selected from the group consisting of a jar, glass, cup and bowl.

9. An aromatic container heater assembly, as recited in claim 1, wherein said container further comprises a material selected from the group consisting of glass, metal and ceramic.

10. An aromatic container heater, as contained in claim 1 wherein the flexible and configurable conductor assembly partially wraps around the container.

11. An aromatic container heater, as contained in claim 1 wherein the flexible and configurable conductor assembly wraps around the container once.

12. An aromatic container heater, as contained in claim 1 wherein the flexible and configurable conductor assembly wraps around the container a multiple number of times.

* * * * *